United States Patent [19]

Nieminen

[11] 4,198,566
[45] Apr. 15, 1980

[54] MOTION MECHANISM OF X-RAY FILM IN PANORAMIC RADIOGRAPHY

[75] Inventor: Timo Nieminen, Helsinki, Finland

[73] Assignee: Den-Tal-Ez Mfg. Co., West Des Moines, Iowa

[21] Appl. No.: 9,686

[22] Filed: Feb. 5, 1979

Related U.S. Application Data

[63] Continuation of Ser. No. 870,621, Jan. 19, 1978, abandoned.

[30] Foreign Application Priority Data

Jan. 24, 1977 [FI] Finland .................................. 770210

[51] Int. Cl.$^2$ ............................................... G11B 1/00
[52] U.S. Cl. .................................. 250/439 P; 250/468
[58] Field of Search ...................... 250/439 P, 468, 490

[56] References Cited
U.S. PATENT DOCUMENTS 2,798,958  7/1957  Hudson ............................ 250/439 P
3,867,636  2/1975  Miyahara ......................... 250/439 P

*Primary Examiner*—Craig E. Church
*Attorney, Agent, or Firm*—Rudolph L. Lowell; G. Brian Pingel

[57] ABSTRACT

This invention relates to a motion mechanism for moving an X-ray film in a panoramic X-ray machine in a predetermined pattern and rate of travel relative to a source of radiation. The mechanism includes a cassette holder on which is carried a rotatable rod or roller driven by a traction wheel, a lever assembly for changing the drive angle between the traction wheel and the rod and a moving or rotatable supporting column or structure on which the motion mechanism is mounted. The panoramic X-ray machine also has a radiation source suspended from one end of the supporting structure at a position opposite the cassette holder. The object o patient to be radiographed is placed between the radiation source and the cassette holder and the supporting structure is rotated at a selected rotational speed about the object.

6 Claims, 2 Drawing Figures

MOTION MECHANISM OF X-RAY FILM IN PANORAMIC RADIOGRAPHY

This is a continuation of application Ser. No. 870,621, filed Jan. 19, 1978 now abandoned.

BACKGROUND OF THE INVENTION, INCLUDING CERTAIN OBJECTS THEREOF

In the panoramic tomographic radiography technique, a layer of certain thickness of the object is visible on the X-ray film. This is the so-called picture layer the form, position and thickness of which can be varied by the geometry involved with the radiography of the object. Normally in this photo technique, the radiation source and the film move relative to the patient who remains stationary during the radiography. The desired point or zone to be radiographed is pictured accurately on the film when the film speed is the same as the speed of the projection spot on the surface of the film to be pictured.

The known arrangements for turning or moving an X-ray film tend to be rather complicated so as to be easily moved or upset out of adjustment. However, in attempts to simplify such arrangements by the use of a cylindrical type film cassette, the obtained results are not entirely satisfactory and in many instances tend to be excessive in cost. In this connection, reference is made to U.S. Pat. Nos. 2,684,446, 2,798,958, 3,536,913 and 3,636,349.

The object of this invention is to develop a motion mechanism for the X-ray film of straight film cassette which is of a simple construction, inexpensive in cost and efficient and practical in operation. Such parts as cog wheels and geared rods, gear belts and wires are eliminated so as to achieve a vibration-free film motion having dependable operation over a long service life.

SUMMARY OF THE INVENTION

The essential feature of the invention is providing for the use of a linearly moveable x-ray film so that a straight film cassette can be used. The cassette holder with its film cassette is moved by a friction drive assembly comprised of a freely rotatable rod mounted on the cassette holder which is in light frictional engagement with an electrically driven traction wheel that is mounted on the supporting structure for movement relative to the rotatable rod such that the angle formed by the axes of the traction wheel and the rotatable rod are varied during the panoramic radiography.

DESCRIPTION OF THE INVENTION

Certain parts of the motion mechanism of this invention that are particularly connected with other mechanisms and performances of the panoramic x-ray machine have been omitted from the drawings for the purpose of clarity and convenience of description.

Figure 1:
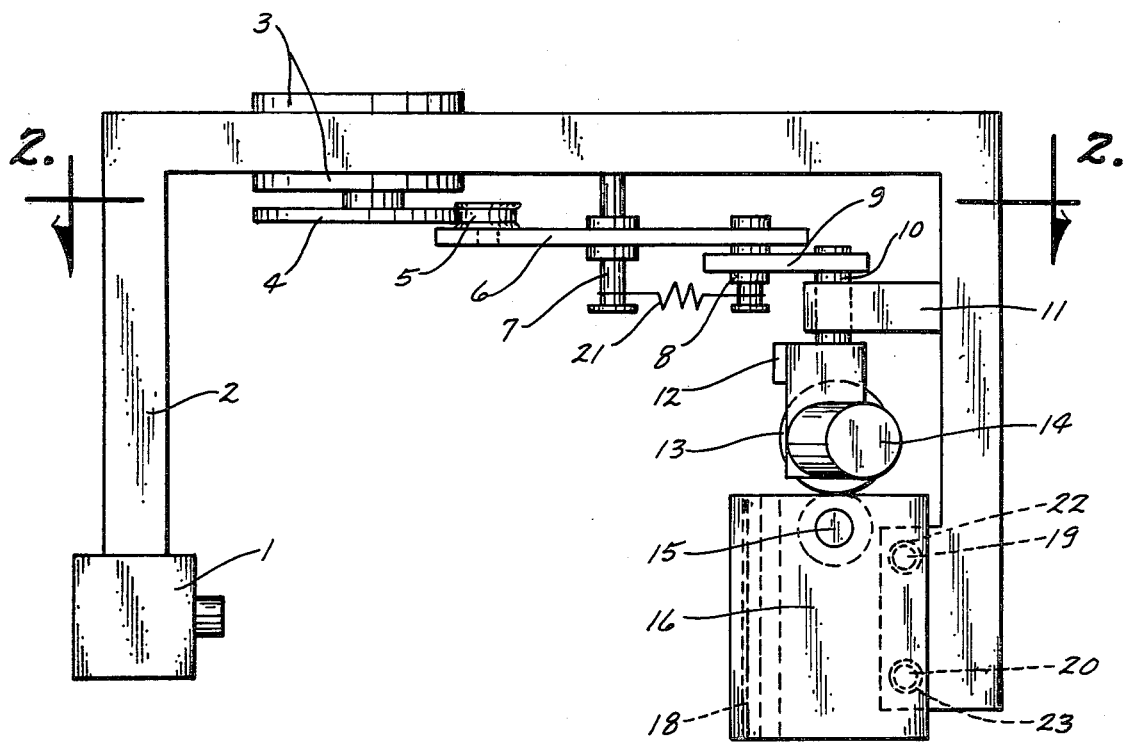
FIG. 1 is a schematic illustration showing the assembly relation of the film motion mechanism with the source of radiation.
Figure 2:
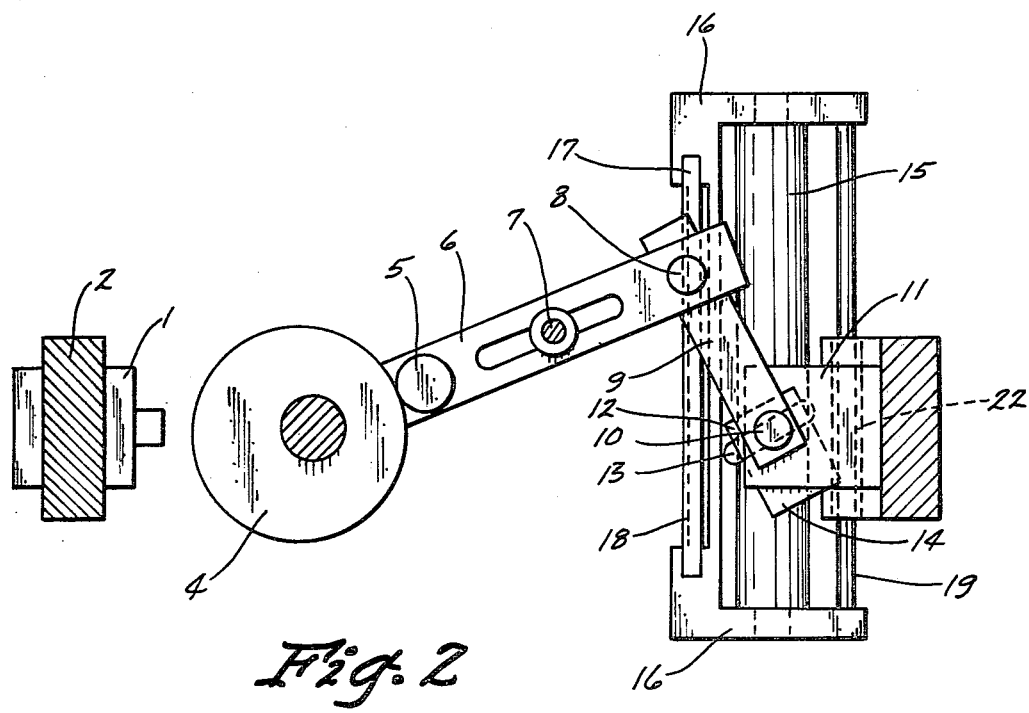
FIG. 2 is a sectional view taken on the line 2—2 in FIG. 1.

With reference to FIG. 1, a radiation source 1 is suspended from a supporting column or structure 2 of a generally inverted U-shape. The base portion of the supporting column or structure 2 is rotatably mounted on a base member 3. A steering or cam plate 4 secured to the base 3 is operatively associated with a friction wheel or cam follower 5 that is rotatably mounted on one end of a slidable lever 6 for movement in a following relation with the peripheral edge of the steering or cam plate 4. A steering plug or stub shaft 7 suspended from the base of the supporting structure 2 is in a lost motion connection with the sliding lever 6 to permit linear movement of the lever 6 in a direction radially of the cam plate 4. The opposite end of the sliding lever 6 is pivotally attached by a plug or connecting pin 8 to the free end of a lever 9, the opposite end of which is rigidly or firmly attached to an axis or stub shaft 10 which in turn is rigidly attached to a base or block member 12. The shaft 10 is rotatably carried in a lateral extension 11 on the supporting structure 2. A spring 21 secured to and extended between the plug 8 and stub shaft or plug 7 yieldably urges the cam follower 5 into engagement with the peripheral edge of the cam plate 4.

The base or block member 12 rotatably supports a traction wheel 13 which is rotated or driven by an electric motor 14 that is also mounted on the block member 12. The traction wheel 13 is in resting or light frictional engagement with a freely rotatable rod 15 both ends of which are rotatably mounted in a cassette holder 16. A film cassette 17 which contains x-ray film 18 is releasably attached to the cassette holder 16. Rigidly carried on the cassette holder 16 is a pair of bearing axes or guide rods 19 and 20 which are slidably supported in linear bearings 22 and 23 carried in the supporting structure 2. The cassette holder 16 is thus moveable linearly in relation to the supporting structure 2 in a direction transversely of the radiation source 1.

It is seen, therefore, that the above described motion mechanism through the freely rotatable rod or roller 15 and traction wheel 13 provides for a controlled motion of the x-ray film in a panoramic x-ray machine. Thus the peripheral speed of the traction wheel 13 is divided into two components relative to the peripheral surface of the freely rotating rod 15, namely, a first component located in the direction of rotation of the rod 15, namely, tangential thereto, which functions to rotate the rod; and a second component which is perpendicular to the rotational component. This second component is located or extends lengthwise in relation to the rod 15 so as to tend to move the rod in an axial direction. Since the freely rotatable rod 15 is attached to the cassette holder 16 with the axis thereof parallel to the plane of the x-ray film 18 a proper synchronism of the film with the source of radiation can be obtained by having the axial component of the peripheral velocity of the traction wheel 13 the same as the desired linear speed of the x-ray film 18. by virtue of the light frictional engagement between the traction wheel 13 and rod 15 the motion mechanism is substantially vibration free and effective to provide an accurate film movement. Since the frictional engagement between the freely rotatable rod 15 and the traction wheel 16 is what might be termed a "light" or "resting" friction the surface of the traction wheel is not exposed to any excessive strain so that the motion mechanism in its entirety is both solid and reliable.

With the supporting structure 2 rotating around the base 3, the friction wheel or cam follower 5 on the sliding lever 6 follows the outer edge of the cam plate 4 so as to cause a linear movement of the sliding lever 6. In response to this sliding movement of the lever 6, the pivoted or swiveling lever 9 is angularly moved predetermined amounts relative to the axis of the stub shaft 10. Since the lever 9, stub shaft 10 and block member 12 are rotatable as a unit on the lateral extension 11, the traction wheel 13 is also pivoted so as to vary the angle of its rotational axis with the rotational axis of the roller 15. This turning movement of the traction wheel 13 relative to the rod 15 can be varied by varying the form of the steering or cam plate 4. A synchronous motor may be substituted for the electric motor 14 to turn the traction wheel 13 so that the rotational speed of the traction wheel 13 may be maintained accurately constant to in turn maintain a controlled exactness in the movements of the motion mechanism.

It is apparent that the traction wheel 13 can also be driven by devices other than an electric motor, for example, through an appropriate transmission of rotational movement of the supporting structure 2 around the base 3. Also the lever mechanism for adjusting the traction wheel 13 relative to the rod 15 may be varied. It is to be further understood that modifications and variations can be made in the described preferred embodiment of the invention all within the scope of the invention as defined by the appended claims.

I claim:
1. A panoramic X-ray machine comprising:
   (a) a base member;
   (b) a supporting structure rotationally mounted intermediate the ends thereof upon said base member;
   (c) an X-ray source attached to one end of said rotatable supporting structure;
   (d) an X-ray film cassette holder attached to the opposite end of said rotatable supporting structure, said cassette holder adapted to hold a film cassette for linear movement during radiographic exposure;
   (e) means for rotationally driving said rotatable supporting structure about said base member; and
   (f) means for driving the film cassette held by said film cassette holder in a linear direction relative to said rotatable supporting structure, said film cassette driving means comprising:
      (1) a rod mounted on said film cassette holder with the longitudinal axis thereof parallel to the plane of the film cassette, said rod mounted for rotation about the longitudinal axis thereof;
      (2) a traction wheel in frictional driving engagement with said rotatable rod; and
      (3) means for rotatably driving said traction wheel such that the rotational axis of said traction wheel is varied in a predetermined angular relation with the longitudinal axis of said rotatable rod;

such that the linear speed of the film cassette relative to said film cassette holder during radiographic exposure is varied in a predetermined manner which is dependent upon the angle between the longitudinal axis of said rotatable rod and the rotational axis of said traction wheel.

2. The machine of claim 1 wherein:
   (a) said traction wheel is driven in a predetermined synchronous relation with the rotational movement of said X-ray source attached to said rotatable supporting structure.

3. The machine of claim 1 wherein:
   (a) said means for rotatably driving said traction wheel varies the angle between the longitudinal axis of said rotatable rod and the rotatable axis of said traction wheel in a manner which is dependent upon the angular position of said X-ray source relative to the axis of rotation of said rotatable supporting structure.

4. The machine of claim 1 wherein said means for rotatably driving said traction wheel includes means on said rotatable supporting structure for pivotally mounting said traction wheel, said mounting means comprising:
   (a) a first lever slidably mounted on said rotatable support structure, said first lever having a first end and a second end;
   (b) cam plate means affixed to said base member;
   (c) cam follower means mounted upon the first end of said first lever in contact engagement with said cam plate means; and
   (d) a second lever having a first end pivotally connected to the second end of said first lever, and a second end connected to said traction wheel.

5. The machine of claim 4 wherein:
   (a) the axis of said cam plate means is coincident with the rotational axis of said rotatable supporting structure.

6. The machine of claim 4 including:
   (a) lost motion means intermediate the first and second ends of said first lever.

* * * * *